United States Patent
Feilkas et al.

(10) Patent No.: US 7,820,446 B2
(45) Date of Patent: Oct. 26, 2010

(54) SYSTEM FOR TRACKING A SPATIAL POSITION OF AN OBJECT VIA A TRACKING SYSTEM

(75) Inventors: Thomas Feilkas, Grafing (DE); Hansjörg Huber, München (DE)

(73) Assignee: BrainLAB AG, Feldkirchen (DE)

( * ) Notice: Subject to any disclaimer, the term of this patent is extended or adjusted under 35 U.S.C. 154(b) by 1377 days.

(21) Appl. No.: 11/283,501

(22) Filed: Nov. 18, 2005

(65) Prior Publication Data

US 2006/0140464 A1   Jun. 29, 2006

Related U.S. Application Data

(60) Provisional application No. 60/645,397, filed on Jan. 19, 2005.

(30) Foreign Application Priority Data

Nov. 18, 2004   (EP)   .................................. 04027430

(51) Int. Cl.
*G01N 33/00* (2006.01)
(52) U.S. Cl. .............................. 436/56; 422/50; 422/55; 422/99
(58) Field of Classification Search ................... 436/56; 422/50, 55, 99
See application file for complete search history.

(56) References Cited

U.S. PATENT DOCUMENTS

| | | | |
|---|---|---|---|
| 4,178,735 A | | 12/1979 | Jackson |
| 4,349,031 A | | 9/1982 | Perlin |
| 5,224,373 A | * | 7/1993 | Williams et al. ........... 73/29.02 |
| 5,413,092 A | | 5/1995 | Williams, III et al. |
| 5,524,643 A | | 6/1996 | Faries, Jr. et al. |
| 5,588,430 A | | 12/1996 | Bova et al. |
| 5,816,252 A | | 10/1998 | Faries, Jr. et al. |

FOREIGN PATENT DOCUMENTS

| | | |
|---|---|---|
| EP | 0 566 861 A1 | 3/1993 |
| WO | 99/04719 | 2/1999 |
| WO | 99/40869 | 8/1999 |

* cited by examiner

*Primary Examiner*—Sam P Siefke
(74) *Attorney, Agent, or Firm*—Renner, Otto, Boisselle & Sklar, LLP

(57) ABSTRACT

A transparent marker casing for use with a tracking system, comprising a material that is transparent to radiation emanating from at least one marker, wherein the marker casing is formed such that it at least partially surrounds the at least one marker. The casing can include a moisture sensor that can detect moisture or liquid on a surface of the casing and provide a signal indicative of the presence of moisture.

12 Claims, 5 Drawing Sheets

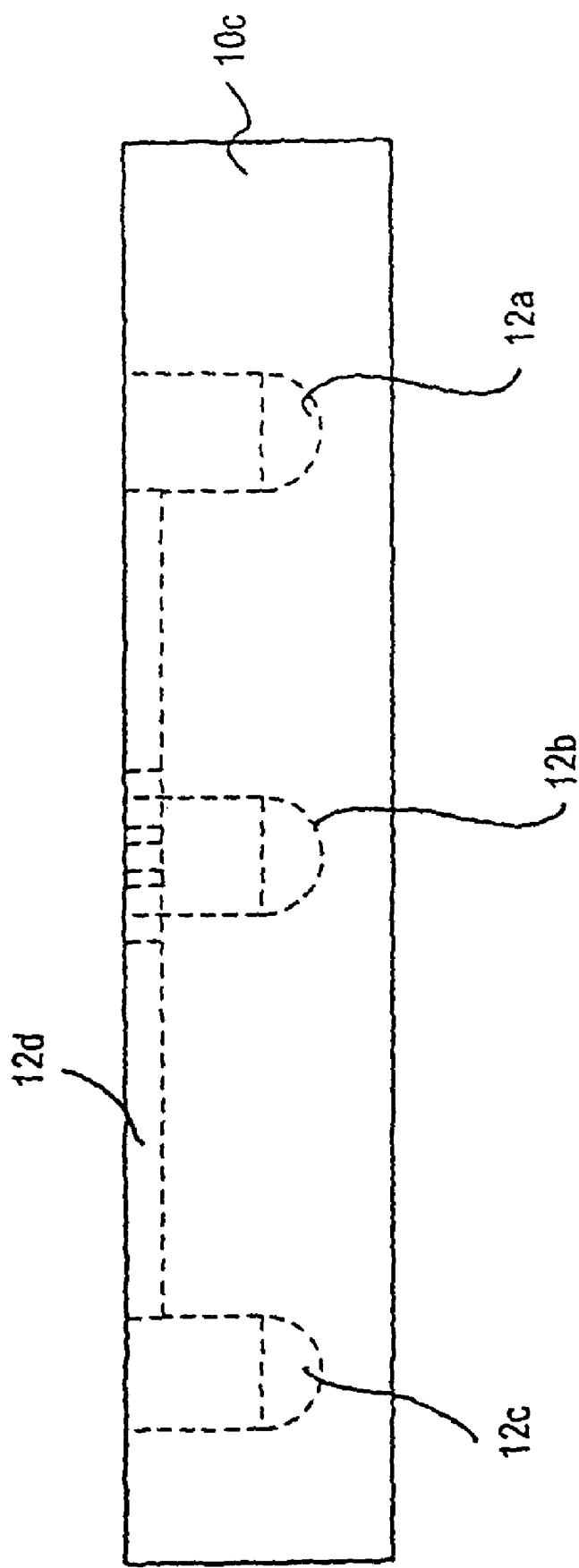

SYSTEM FOR TRACKING A SPATIAL POSITION OF AN OBJECT VIA A TRACKING SYSTEM

RELATED APPLICATION DATA

This application claims priority of U.S. Provisional Application No. 60/645,397 filed on Jan. 19, 2005, which is incorporated herein by reference in its entirety. European Patent Application No. 04027430.0 is incorporated herein by reference in its entirety.

FIELD OF THE INVENTION

The present invention relates to markers used with tracking or navigation systems and, more particularly, to a transparent casing for markers used with medical navigation systems.

BACKGROUND OF THE INVENTION

Tracking systems serve to determine and track positions of devices by detecting (e.g. by means of a camera) a position of markers attached to the device. Medical tracking systems serve to determine a position of an instrument or body part with the aid of markers and/or a reference star attached to the instrument/body part (e.g., the reference star can include the markers). The markers can be passive or active markers. Passive markers reflect light, in particular infrared light (but also, for example, visible or UV light) radiated onto them, while active markers emit light themselves. The position of the markers, in particular the reference star and therefore the instrument or body part attached to the reference star, can be determined with the aid of cameras that detect light emitted by the markers.

The markers typically are spherical markers, but also can exhibit a different structure, such as cubiform, for example. A surface of passive markers generally is formed similar to cats' eyes, with a multitude of small reflecting faces that in turn can be spherical or hemispherical. Thus, a multitude of recesses can be situated on the markers, in which liquid, such as, for example, rinsing liquid, blood or blood smears, can accumulate. These liquids or soils can alter the emission of light from the markers and, as a result, the navigation system may incorrectly calculate the position of the markers. In the case of spherical markers, for example, a center of the marker sphere can be calculated incorrectly if the emitted light (active or reflected light) is changed by marks or drops of liquid situated on the markers. In particular, additional reflections may occur on the surface of the liquid, which impair the emission or light, resulting in calculation errors.

In practical medical applications, the multitude of recesses in markers are problematic, as it is difficult for the practitioner (in particular a physician or nurse) to recognize whether the reflections are due to liquid or marks on the marker. The practitioner thus does not know whether it is necessary to clean the markers. In particular, the recesses spread the liquid out on the surface of the marker and, thus, make it more difficult to determine whether the marker should be cleaned.

SUMMARY OF THE INVENTION

A transparent marker casing can be provided that minimizes or eliminates problems related to substances accumulating on the marker surface. At least portions of the marker casing, and preferably the entire marker casing, can be formed from a transparent material. The transparent material can be transparent to radiation (e.g., optical radiation) that is detected by cameras of a navigation system for determining the position of the markers. The radiation can emanate from the markers due to reflection (passive markers) or emission (active markers) from the makers. The material can be transparent to infrared radiation and/or visible light.

As used herein, transparent is defined as a degree of transmission of radiation of 80% or more, preferably 90% or more, more preferably 95% or more, and most preferably 99% or more. Transparent also means that a degree of reflection for the radiation is about 20% or less, preferably 10% or less, more preferably 5% or less, and most preferably 1% or less. Transparent also means that a degree of absorption for the radiation is 20% or less, preferably 10% or less, more preferably 5% or less and most preferably 1% or less.

The marker casing can exhibit a surface that does not accommodate or otherwise pick up liquid, does not absorb liquid, and/or does not attract or hold liquid due to surface tension effects. The marker casing can be formed such that it exhibits a smooth surface, in particular portions can have an even surface. The surface can be formed to be liquid-resistant, in particular hydrophobic. Specifically, the surface and/or the material of the marker casing can be formed from a polymer, from polyvinylchloride, from polyethylene, from polypropylene, polycarbonate or from tetrafluoroethylene or a mixture of the aforementioned. The surface can be hydrosiliconised. The marker casing also can be formed such that it is transparent in the infrared range but not transparent in the visible range. Specifically, the casing can be reflective and/or appear white in the visible light range, so as to enable a practitioner to easily recognize soiling of the marker casing, while infrared radiation emitted and/or reflected by the markers passes through the marker casing.

The marker casing can be formed in the manner of a housing that at least partially and preferably completely surrounds a marker or a marker array (e.g., the markers of a reference star). The marker casing also can partially envelope the marker in the manner of a protective layer, which provides a smooth surface to the marker. The protective layer can be applied directly to the surface of the marker.

The marker casing preferably has a stable, in particular rigid, surface structure to enable easy recognition of surface soils and to enable easy cleaning of the casing. The marker casing can be a preformed structure and can be formed from a thin material, such as a plastic material, for example. Thin, as used herein, means less than 2 millimeters (mm), preferably less than 1 mm, and more preferably less than 0.5 mm. The marker casing can include reinforcements, notches or folds, to stabilize the structure. These reinforcements, notches or folds can be arranged such that they do not interfere with the detection of the markers.

The marker casing can be formed with a preformed structure that includes one or more recesses to accommodate one or more markers, a reference star comprising markers, or a combination of two markers (e.g. for a pointer), for example. A reference star includes at least two or three markers that are connected by mechanical connecting members such that the markers span a plane (three markers) or a 3D structure (four or more markers). In particular, the recess in the structure can be formed such that the markers or the reference star are embedded. In other words, once the at least one marker or the reference star has been inserted into the recess of the marker casing, a cover (e.g., a flat cover), can seal the recess so as to completely enclose the at least one marker and the recess.

The marker casing can be configured such that at least one marker and/or a reference star can be inserted into and removed from the marker casing. The marker casing can include the aforementioned seal and/or a cover that also can be transparent and preferably formed from the same material. The seal can be configured such that the at least one marker and/or reference star situated in the cavity only can be removed from the cavity when the seal is opened. The casing can be configured such that the opening forming the cavity is sealed by the seal. The seal can be configured such that no liquids (e.g., soiling liquids) can enter the casing.

The marker casing can include a means for holding the at least one marker and/or reference star at a predetermined position. To this end, a clamping or pressing fit and/or a latching mechanism can be provided that holds the at least one marker and/or reference star when the at least one marker and/or reference star is inserted into the marker casing, in particular into the cavity. The seal mentioned above also can be formed to hold the at least one marker and/or reference star at a particular position.

The marker casing can include a sensor in order to recognize or verify foreign substances that can impair radiation emanating from the markers. In particular, the sensor can be formed such that it can detect or verify the presence of liquids or foreign substances on the surface of the marker casing, such as the outer surface of the marker casing. The sensor can be formed such that when it has verified a foreign substance or a liquid, it outputs a detectable signal, such as an optical or electrical signal. In this way, the navigation system can be warned that radiation emitted from the markers may be impaired. The sensor or the means for verifying moisture or foreign substances also can be formed such that it is optically altered, wherein the observation cameras can detect the alteration. Additional warning electronics can thus be avoided. The surface of the marker casing can be configured such that it changes color when moist (e.g., the marker casing becomes black and/or no longer transparent to the light, such as IR light, when it comes into contact with liquid). This can ensure that incorrect navigation is not performed, since the user or practitioner can immediately recognize that the emission of the markers may be impaired. The user or practitioner can clean the marker casing to remove the soil, thereby restoring proper operation of the markers.

The transparent marker casing can be provided separate from the markers or reference star. The markers or reference star can, however, also be provided in combination with the marker casing. Specifically, a system including a marker and marker casing can be formed such that the transparent marker casing is formed fixedly, in particular fused, around the at least one marker or reference star, or the at least one marker and/or reference star can be molded into a transparent marker casing. The at least one marker and/or reference star can be molded into a transparent plastic mass, for example.

A tracking system (also called navigation system) can be provided that includes a reference star and cameras for detecting optical radiation from the markers of the reference star, wherein at least one of the markers and/or the reference star can be surrounded by the transparent marker casing. In the case of passive markers, a marker illuminator can be provided that emits light, in particular IR light, onto the markers, which reflect said light. The tracking system for navigating a medical instrument or for detecting the position of a body part can be formed such that a warning signal can be provided when a sensor detects foreign substances or liquids that impair detection of optical radiation from the markers, as discussed herein. The tracking system also can be used in other areas, such as, for example, virtual reality (e.g. computer or video games), robot guidance, sports media, etc.

BRIEF DESCRIPTION OF THE DRAWINGS

FIG. 5 shows a lateral view of the embodiment of FIG. 1.

DETAILED DESCRIPTION

Figures 1A, 1B:
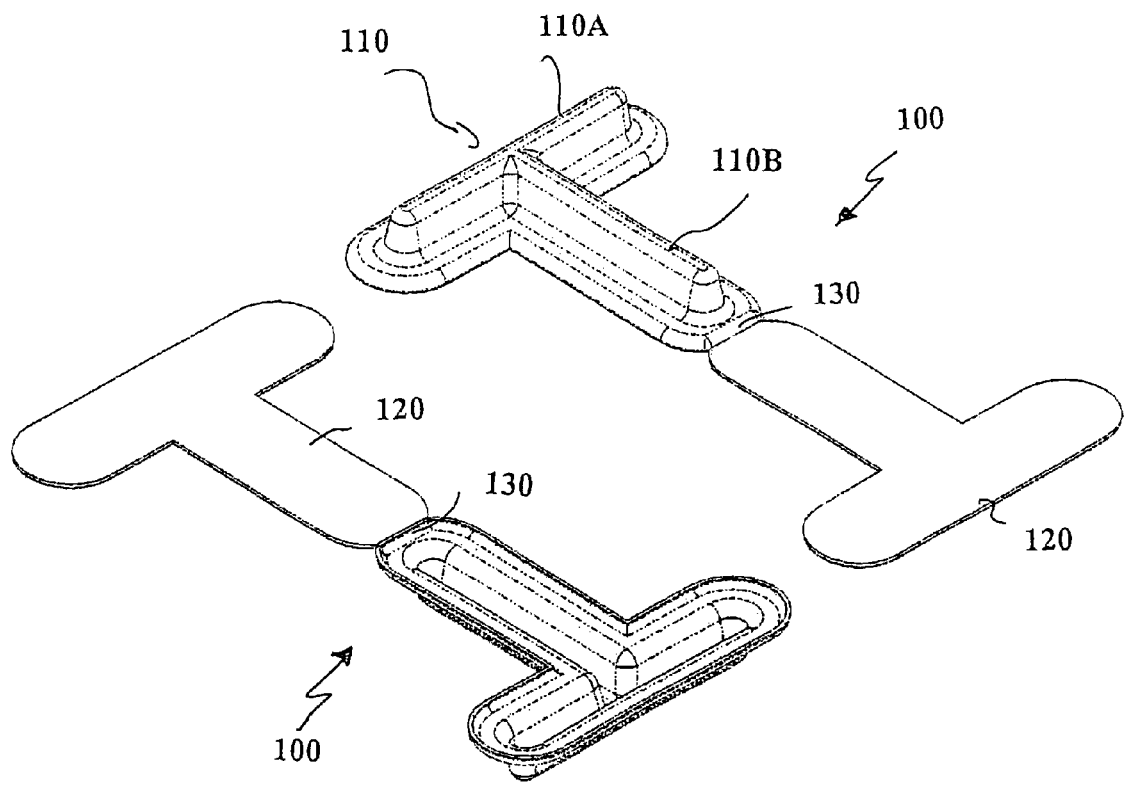
FIGS. 1A and 1B show a transparent marker casing in accordance with an embodiment of the invention.

FIGS. 1A and 1B show a transparent marker casing 100 that includes a T-shaped structure 110 formed by two shell-like longitudinal trenches 110A and 110B, which merge into each other. The shape of the trenches flattens towards an edge. A cover 120 is connected via a hinge 130 to a longitudinal trench 110B at the end facing away from the longitudinal trench 110A. The cover is preferably formed flat and/or even and seals the T-shaped opening formed by the two longitudinal trenches 110A and 110B. The longitudinal trenches 110A and 110B represent a recess, in particular a shell-like recess. The marker casing 100, in particular all the components such as the cover 120, the longitudinal trenches 110 and the hinge 130, are preferably formed from polypropylene, such as used for pharmaceutical packaging, for example. The film thickness is preferably less than 1 mm and more preferably less than 500 µm (e.g., 300 µm).

The marker casing preferably is formed from a film by means of a deep drawing method. The marker casing 100 and the raw materials used for the casing preferably comply with the relevant BgVV, EC and FDA provisions for the manufacture of pharmaceutical packaging. Preferably, the biocompatibility of the film is guaranteed. The film material preferably is configured such that a crystal melting range in accordance with ISO 3146 is above 100 degrees C. The mechanical tensile strength in accordance with ISO 527-3 preferably is over 10 N/mm$^2$. The surface finish in accordance with DIN 67530 preferably is greater than 70 percent, and more preferably greater than 90 percent. The haze in accordance with ASTM D-1003 preferably is less than 30 percent, and more preferably less than 20 percent.

Figure 2:
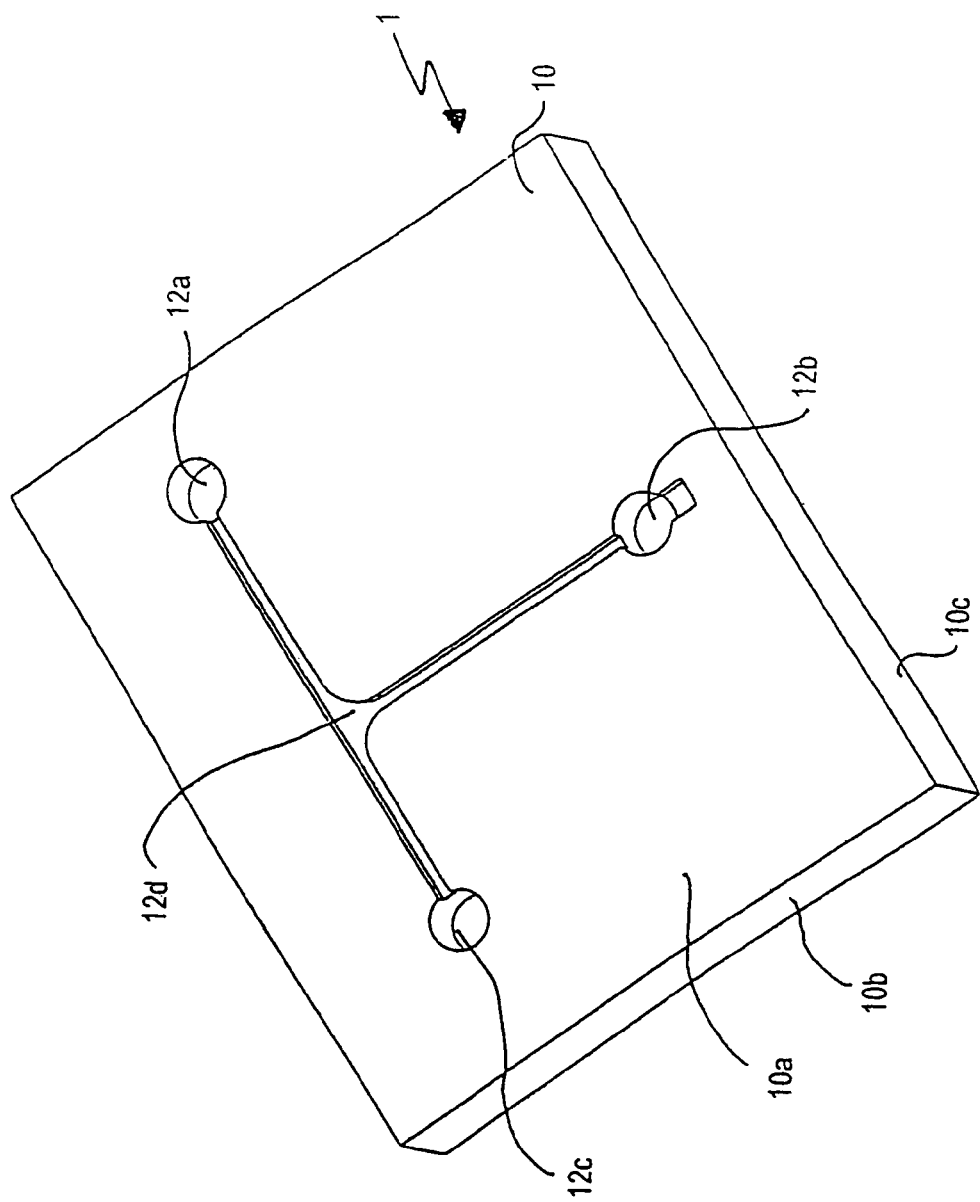
FIG. 2 shows a negative deep drawn mold for a transparent marker casing in accordance with another embodiment of the invention.

In the deep drawn mold in accordance with FIG. 2 for a transparent marker casing, a cavity preferably is formed that includes cavities 12a, 12b and 12c for marker spheres. The cavities preferably are formed to be cylindrical to accommodate corresponding cylindrical recesses in the marker casing, thereby enabling the marker spheres to be easily introduced onto a mount, for example. The cavity 12 preferably includes a portion 12d which, when the marker casing is molded using a deep drawn mold, forms a channel-like recess for inserting the connecting arms of the reference star for the individual marker spheres. In the embodiment shown in FIG. 1, with a marker casing manufactured with said channel-like recess, an entire reference star can thus be inserted into the recess corresponding to the recess 12. The marker casing manufactured in this way, just as the embodiment in accordance with FIG. 1, can accommodate a reference star having a so-called T geometry.

The markers need not be spherical, but also can be formed flat, for example platelet-like or as a disc. The flat markers preferably exhibit a rough surface including a multitude of reflective bumps.

The invention has applications in knee-joint crucial ligament operations (ACL operations), tracking or navigation applications such as the so-called Vector Vision Spine (i.e., a navigation application in the area of the spine), the so-called Vector Vision Trauma (VV Trauma), and in radiotherapy, for example. Other medical and non-medical applications relate to any manner of analyzing and detecting movement by bodies and devices. Examples are video games, television and film animation, virtual reality, gait analysis (in particular in humans or animals), body movement analysis (sports medicine), analyzing prosthetics, neuroscience, product design, etc.

Figure 3:
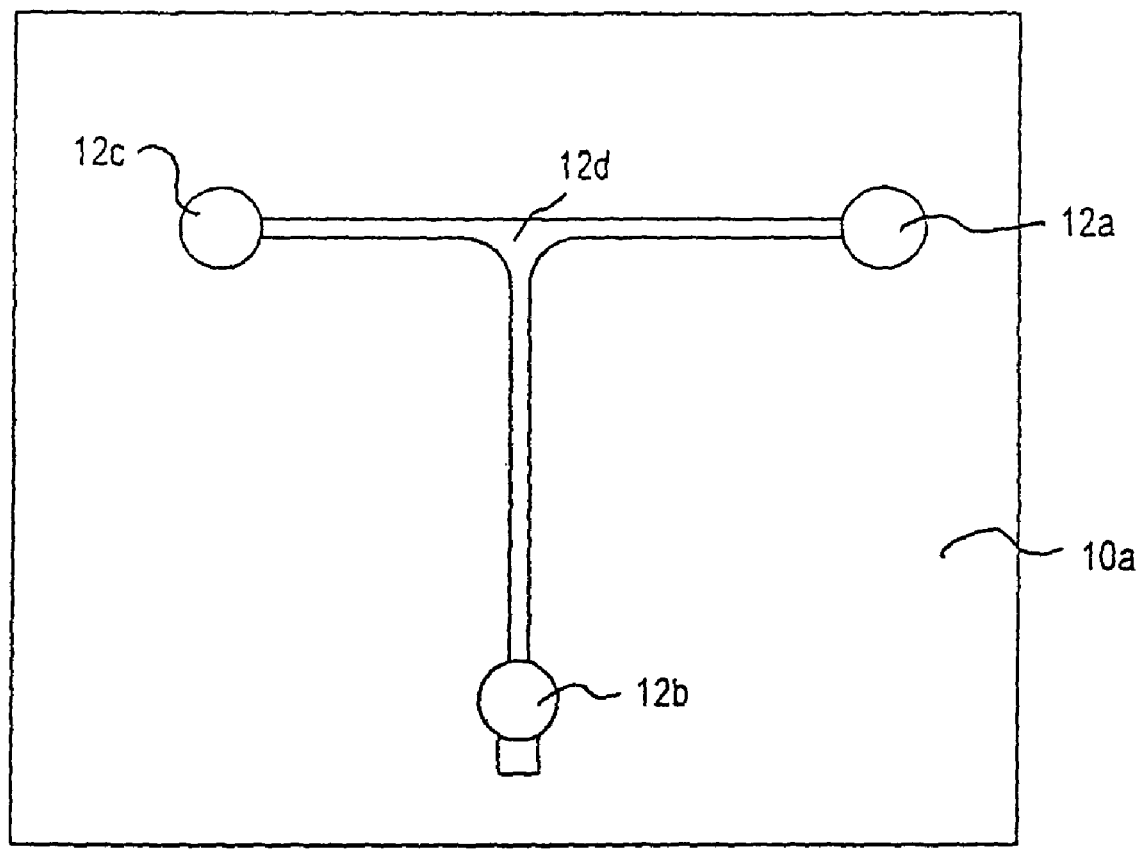
FIG. 3 shows a top view onto the embodiment of FIG. 1.

FIG. 3 shows a top view of the deep drawn mold of FIG. 2. Identical parts are provided with the same reference numerals.

Figure 4:
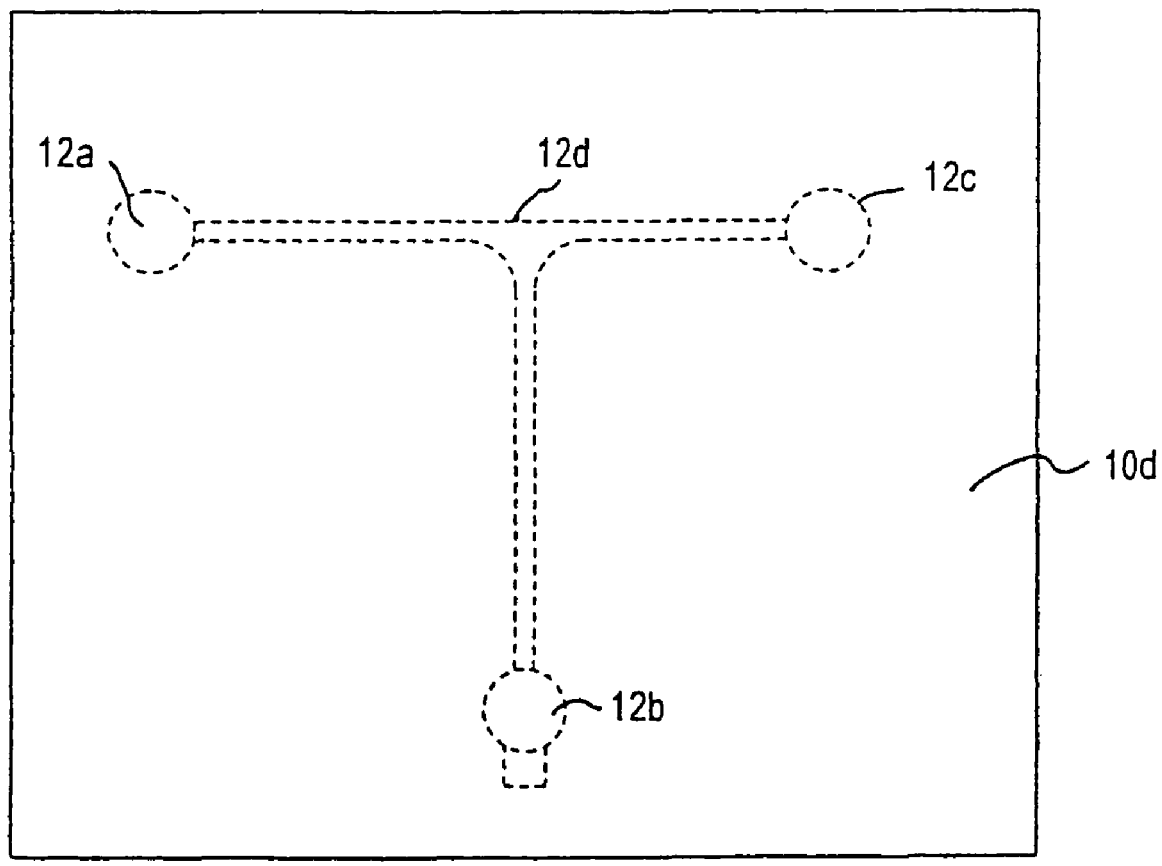
FIG. 4 shows an underside view onto the embodiment of FIG. 1.

FIG. 4 shows a view of the deep drawn mold from below, wherein identical parts are provided with the same reference numerals. The underside of the block is indicated by the reference numeral 10d. The cavity 12, including the components 12a, 12b, 12c and 12d, are indicated by a broken line, since as opposed to FIGS. 2 and 3, it does not open towards the surface 10d. In FIGS. 2 and 3, the cavity 12 is indicated by a continuous line, since the surface 10a is interrupted by the cavity 12.

FIG. 5 shows a lateral view of the deep drawn mold of FIG. 2. Identical parts are again provided with the same reference numerals. The cavity 12, including the components 12a, 12b, 12c and 12d, are again indicated by a broken line, since it does not open towards the side face 10c. The deep drawn mold shown in FIGS. 2 through 5 is a negative mold.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A system for tracking a spatial position of an object via a tracking system, comprising:
at least one marker trackable by the tracking system;
a transparent marker casing comprising a material that is transparent to radiation emanating from the at least one marker, wherein the marker casing is formed such that it at least partially surrounds the at least one marker;
a moisture sensor that can detect moisture or liquid on a surface of the casing and provide a signal indicative of the presence of moisture; and
the tracking system, wherein the tracking system is communicatively coupled to the moisture sensor and configured to provide a warning signal when the moisture sensor detects moisture on the surface of the casing.

2. The system as set forth in claim 1, wherein the material exhibits a surface that does not accommodate liquid.

3. The system of claim 2, wherein the surface is a smooth and/or liquid-resistant surface.

4. The system as set forth in claim 1, wherein the marker casing comprises a preformed, stable structure made of thin plastic material.

5. The system as set forth in claim 1, wherein the marker casing is formed to at least partially surround a reference star comprising markers.

6. The system as set forth in claim 1, wherein the casing further comprises a recess in which at least one marker can be accommodated so as to at least partially surround the at least one marker with the casing.

7. The system as set forth in claim 1, wherein the casing can be sealed and the at least one marker and/or a reference star can be inserted or removed from the casing by opening the seal.

8. The system as set forth in claim 1, wherein the casing is formed such that when the at least one marker is in the casing, the at least one marker is positionally fixed relative to the casing.

9. The system as set forth in claim 1, wherein the signal is an optically altered signal detectable by the tracking system.

10. The system as set forth in claim 1, wherein the signal includes a change in color of the marker casing, said color change being visually detectable by the human eye and/or the tracking system.

11. The system as set forth in claim 1, further comprising cameras for detecting optical radiation from the markers, wherein the at least one marker is surrounded by the marker casing.

12. The system casing according to claim 1, wherein the surface is transparent to visible light.

* * * * *